US010166174B2

(12) United States Patent
Cunningham et al.

(10) Patent No.: US 10,166,174 B2
(45) Date of Patent: Jan. 1, 2019

(54) WET WIPES FOR PERSONAL CARE

(71) Applicant: Kimberly-Clark Worldwide, Inc., Neenah, WI (US)

(72) Inventors: Corey T. Cunningham, Larsen, WI (US); JongChon Kim, AnYang (KR); JungHak Kim, Hwaseong-si (KR); HwaJun Lee, Yongin-si (KR); SangSoo J. Lee, Gwangju-si (KR); SangHa Park, Yongin-si (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 422 days.

(21) Appl. No.: 15/101,382

(22) PCT Filed: Dec. 2, 2014

(86) PCT No.: PCT/US2014/068219
§ 371 (c)(1),
(2) Date: Jun. 2, 2016

(87) PCT Pub. No.: WO2015/084880
PCT Pub. Date: Jun. 11, 2015

(65) Prior Publication Data
US 2016/0303002 A1 Oct. 20, 2016

Related U.S. Application Data

(60) Provisional application No. 61/911,241, filed on Dec. 3, 2013.

(51) Int. Cl.
A61K 8/02 (2006.01)
A61Q 19/00 (2006.01)
A47K 10/42 (2006.01)
B65B 5/06 (2006.01)
A61K 8/73 (2006.01)
A61K 8/86 (2006.01)
A61K 8/04 (2006.01)
A61K 8/34 (2006.01)
A61Q 19/10 (2006.01)
A47K 10/32 (2006.01)

(52) U.S. Cl.
CPC .............. A61K 8/027 (2013.01); A47K 10/42 (2013.01); A61K 8/0208 (2013.01); A61K 8/0241 (2013.01); A61K 8/0279 (2013.01); A61K 8/04 (2013.01); A61K 8/34 (2013.01); A61K 8/731 (2013.01); A61K 8/732 (2013.01); A61K 8/86 (2013.01); A61Q 19/005 (2013.01); A61Q 19/10 (2013.01); B65B 5/06 (2013.01); A47K 2010/3266 (2013.01); A61K 2800/412 (2013.01); A61K 2800/56 (2013.01); A61K 2800/87 (2013.01)

(58) Field of Classification Search
CPC ........ A61K 8/027; A61K 8/731; A61K 8/732; A61K 8/86; A61K 8/0208; A61K 8/0241; A61K 8/0279; A61K 8/04; A61K 8/34; A61K 2800/412; A61K 2800/56; A61K 2800/87; A47K 10/42; A47K 2010/3266; A61Q 19/05; A61Q 19/10; B65B 5/06
See application file for complete search history.

(56) References Cited

U.S. PATENT DOCUMENTS

| | | | |
|---|---|---|---|
| 4,817,790 A | 4/1989 | Porat et al. | |
| 4,840,746 A | 6/1989 | Shiozaki et al. | |
| 5,534,265 A | 7/1996 | Fowler et al. | |
| 5,824,323 A | 10/1998 | Fishman | |
| 5,871,756 A | 2/1999 | Jeffcoat et al. | |
| 6,217,889 B1 | 4/2001 | Lorenzi et al. | |
| 6,340,663 B1 | 1/2002 | Deleo et al. | |
| 6,416,751 B1 | 7/2002 | Roulier et al. | |
| 6,458,372 B1 | 10/2002 | Scordamaglia-Crockett et al. | |
| 6,737,068 B2 | 5/2004 | Durden | |
| 6,903,057 B1 | 6/2005 | Tsaur | |
| 6,906,016 B1 | 6/2005 | Tsaur | |
| 7,332,179 B2 | 2/2008 | Kistler et al. | |
| 7,446,082 B2 * | 11/2008 | Kilkenny | A01N 37/36 510/191 |
| 7,455,849 B2 | 11/2008 | Utschig et al. | |
| 7,571,812 B2 | 8/2009 | Francis | |
| 7,736,632 B2 | 6/2010 | Gorman | |
| 8,318,654 B2 * | 11/2012 | Hoffman | A01N 25/34 510/186 |
| 8,877,316 B2 * | 11/2014 | Hasenoehrl | A44B 18/0011 428/88 |

(Continued)

FOREIGN PATENT DOCUMENTS

| CN | 1283104 A | 2/2001 |
|---|---|---|
| CN | 1308519 A | 8/2001 |

(Continued)

Primary Examiner — David Walczak
(74) Attorney, Agent, or Firm — Kimberly-Clark Worldwide, Inc.

(57) ABSTRACT

Pre-moistened wiping articles are provided comprising a fibrous web impregnated with a liquid cleaning composition including an unstable dispersion of water, surfactant, and water insoluble polysaccharide particles such as natural starch and/or microcrystalline cellulose. Due to the instability of the dispersion the particles primarily reside on the surface of the fibers forming the fibrous web and are freely released from the web as a result of the mechanical and hydraulic forces associated with use of the article. The pre-moistened wiping articles are suitable for use in personal care applications including use as perineal wipes. Embodiments of the invention further include methods of making pre-moistened wiping articles comprising a fibrous web impregnated with the unstable dispersion.

20 Claims, No Drawings

(56) References Cited

U.S. PATENT DOCUMENTS

| | | |
|---|---|---|
| 2002/0192407 A1 | 12/2002 | Hendrix et al. |
| 2003/0031722 A1 | 2/2003 | Cao et al. |
| 2003/0130636 A1 | 7/2003 | Brock et al. |
| 2005/0058674 A1 | 3/2005 | Joseph et al. |
| 2005/0158369 A1 | 7/2005 | Dorschner et al. |
| 2005/0170979 A1 | 8/2005 | Massaro et al. |
| 2007/0032393 A1 | 2/2007 | Patel et al. |
| 2008/0145267 A1 | 6/2008 | Do et al. |
| 2009/0035340 A1 | 2/2009 | Landa et al. |
| 2010/0303910 A1 | 12/2010 | Candolives et al. |
| 2011/0159105 A1 | 6/2011 | Vilinsky |
| 2012/0058165 A1 | 3/2012 | Klofta et al. |
| 2012/0141571 A1 | 6/2012 | Lee et al. |
| 2012/0269743 A1 | 10/2012 | Smith et al. |

FOREIGN PATENT DOCUMENTS

| | | |
|---|---|---|
| EP | 0 735 866 B1 | 2/2001 |
| JP | 10-273418 A | 10/1998 |
| WO | WO 1999/007274 A1 | 2/1999 |
| WO | 2015084880 A1 | 6/2015 |

\* cited by examiner

WET WIPES FOR PERSONAL CARE

This application claims the benefit of priority from U.S. Provisional Application No. 61/911,241 filed on Dec. 3, 2013.

FIELD OF INVENTION

The present invention is related to disposable wiping articles for personal care, and more particularly to pre-moistened wipes suitable for use as perineal wipes.

BACKGROUND

Pre-moistened wipes have been used for personal cleaning for numerous years. In order to improve the cleaning efficiency of the wipes it is common to include aqueous based cleaning compositions containing various surfactants and/or detergents. However, cleaning compositions containing water and surfactant are often perceived as being too viscous and lacking a pleasing feel. In addition, pre-moistened wipes using high amounts of water and/or that readily release high amounts of water can contribute to a user having a prolonged feeling of wetness.

It is also common to include various emollients, skin conditioners, thickeners and other skin benefit agents in order to improve the cleaning efficacy of the wipe and/or the ability of the wipe to reduce skin irritation that sometimes results from cleaning. While the addition of such components increases the viscosity and/or richness of the cleaning composition's hand-feel, many skin benefit agents are hydrophobic and require the use of specific emulsifiers and/or thickening agents to provide a stable cleaning composition. Inclusion of such materials into the pre-moistened wipe often results in a wipe that has an undesirable feel; for example, often leaving the user with a slippery or sticky feeling. Thus, it is difficult to effectively incorporate ingredients into wet wipe formulations which will enable it to be an effective cleaner while still providing a pleasing skin feel, i.e. use of the wet wipe will not produce a feeling of excessive wetness, greasiness, and/or tackiness.

Therefore, in order to address the unmet needs associated with prior wet wipes, the present invention provides a pre-moistened wipe which is a highly effective cleaner and that provides both a pleasing initial feeling as the wipe is applied to the skin and yet which does not leave the consumer with an undesirable lingering feeling of wetness, greasiness and/or tackiness.

SUMMARY OF THE INVENTION

A wet wipe is provided comprising a porous sheet formed from a coherent web of fibers and containing an unstable cleaning composition therein in an amount between 50% and 600% (based upon the dry weight of said porous sheet). In one embodiment, the unstable cleaning composition contained within the wet wipe comprises (based upon the weight of the cleaning composition) (i) greater than 92.0% water, (ii) between 4% and 0.05% surfactant, and (iii) between about 3.0% and about 0.05% water insoluble polysaccharide particles. Due to the instability of the cleaning composition the particles reside on the surface of the fibers forming the porous sheet. However, due to the nature of the particles and the corresponding formulation, they will be freely released from the web as a result of the mechanical and hydraulic forces associated with use of the wet wipe.

In certain embodiments the polysaccharide may comprise a birefringent and/or crystalline polysaccharide such as for example a natural and unmodified polysaccharide selected from the group consisting of starch and microcrystalline cellulose. In certain embodiments the polysaccharide may comprise a starch having a gelatinization temperature in excess of 50° C. In still further embodiments, the particles may have an average particle size between about 1 and about 100 microns.

In an alternate embodiment, the unstable cleaning formulation within the wet wipe may comprise (i) water, (ii) a water soluble alcohol selected form the group consisting of methanol, ethanol, propanol, butanol and pentanol, (iii) between 4% and 0.05% surfactant, and (iv) between about 3.0% and about 0.05% water insoluble polysaccharide particles such as those described herein. In certain embodiments, the ratio of water to alcohol is between 3:1 and 100:1. Again, as noted above, due to the instability of the cleaning composition the particles will reside on the surface of the fibers forming the porous sheet.

In addition, a method of making wet wipes is also provided and comprises the steps of (a) providing a porous fibrous sheet;

(b) providing an unstable aqueous dispersion as described herein;

(c) mixing said unstable aqueous dispersion to generate a substantially homogenous aqueous dispersion;

(d) applying said substantially homogenous aqueous dispersion to said fibrous sheet in an amount between about 50% and 600% based upon the dry weight of said fibrous sheet, thereby forming a wet wipe; and (e) sealing said wet wipes in a container.

In certain aspects, the method is further characterized by maintaining the aqueous dispersion at a temperature at least about 5° C. below the gelatinization temperature of the polysaccharide. For example, in certain aspects the method may further include the steps of (B1) adding the surfactant to the water under heat to form an aqueous solution, (B2) cooling the aqueous solution to a temperature at least 5° C. below the gelatinization temperature of the polysaccharide and then (B3) adding the polysaccharide particles to the aqueous solution to form an unstable aqueous dispersion.

Definitions

Throughout the specification and claims, discussion of the articles and/or individual components thereof is with the following understanding:

The term "comprising" or "including" are inclusive or open-ended and do not exclude additional unrecited elements, compositional components, or method steps. Accordingly, the terms "comprising" or "including" encompass the more restrictive terms "consisting essentially of" and "consisting of."

The term "insoluble" means having a solubility in water of less than 0.1 g/100 g water at a temperature of 50° C. for 24 hours.

As used herein, the term "gelatinization temperature" means the temperature at which the polysaccharide begins to change from an order state to a disordered state as determined by the electrical conductivity method described herein.

As used herein, the term "natural" means a substance that is found in nature.

As used herein, unless expressly indicated otherwise, when used in relation to material compositions the terms "percent", "percent", "weight percent" or "percent by weight" each refer to the quantity by weight of a component as a percentage of the total.

As used herein, the term "stack" is used broadly to include any collection of sheets wherein there is a plurality of individual sheets having surface-to-surface interfaces; this not only includes a vertically stacked collection of individual sheets, but also includes a horizontally stacked collection of individual sheets as well as a rolled or folded collection of continuous sheet material separated by lines of weakness (e.g. perforations).

As used herein "unmodified" means a substance in which the raw or natural chemical structure of the substance has not been significantly modified by a chemical reaction; for the sake of clarity, a substance would not be considered modified by routine processing associated with manipulation of the physical form of the substance, e.g. modification of the size, shape, purity, etc.

As used herein an "unstable dispersion" means a dispersion in which the particles contained within the liquid phase are not supported within the liquid for a period in excess of 24 hours; i.e. a dispersion in which the particles will sink to the supporting solid surface within 24 hours.

As used herein, the term "wet wipe" refers to a fibrous sheet which, during its manufacture, has a liquid applied thereto so that the liquid is retained on or within the fibrous sheet until its utilization by a consumer.

DETAILED DESCRIPTION

Base Sheet

The personal cleaning articles of the present invention include a highly porous wiping substrate having individual openings or interstitial spaces which, in a preferred aspect, collectively form pathways through the thickness of the material via adjacent, inter-connecting spaces or openings. In addition to being highly porous, the wiping substrate desirably has a soft and pleasing hand and remains resiliently compressible when wet. Desirably, the porous wiping substrate is a coherent fibrous sheet having numerous interstitial spaces within the fabric. In this regard, numerous fibrous sheet materials known in the art are suitable for use in the present invention. The fibrous sheets may comprise continuous fibers, stable length fibers, or combinations of the same. In addition, the sheet material may comprise natural fibers (e.g. wood pulp, cotton, bamboo, hemp, etc.), synthetic fibers (e.g. polyolefin, polyester, polyamide, polylactic acid, rayon, lyocell, etc.) or combinations of natural and synthetic fibers. In addition, the fibrous sheets may comprise either woven, knit, or nonwoven fabrics and further the fibrous sheets may be used to form laminates with one or more additional sheet materials. Suitable fibrous sheets will typically have a dry basis weight of from about 25 $g/m^2$ to about 175 $g/m^2$. In certain embodiments, the dry basis weight of the fibrous sheet will be about 35 $g/m^2$ to about 125 $g/m^2$ and in still further embodiments may be between about 35 $g/m^2$ to about 90 $g/m^2$.

In certain embodiments, the fibrous sheet of the present invention can comprise an air-laid nonwoven web. In the air-laying process, fibers are entrained in an air stream, intermingled and then deposited onto a forming screen or wire, usually with the assistance of a vacuum supply. The randomly deposited fibers are then bonded to one another autogenously, such as through the use of heat and/or pressure, or through the use of a binder, such as by the inclusion of binder fibers or the application of adhesive to the web. With respect to air-laid nonwoven webs, suitable wiping substrates include, but are not limited to, meltblown, spunbond, and bonded-carded web materials. By way of non-limiting example, various specific examples of suitable air-laid nonwoven sheets, and methods of making the same, are described in U.S. Pat. No. 3,849,241 to Butin et al., U.S. Pat. No. 4,340,563 to Appel et al., U.S. Pat. No. 4,443,513 to Meitner et al., U.S. Pat. No. 4,548,856 to Ali Kahn et al., U.S. Pat. No. 4,853,281 to Abba et al., U.S. Pat. No. 5,382,400 to Pike et al., U.S. Pat. No. 5,575,874 to Griesbach et al., U.S. Pat. No. 6,224,977 to Kobylivker et al., U.S. Pat. No. 6,811,638 to Close et al., U.S. Pat. No. 6,946,413 to Lange et al., US2004/0192136 to Gusky et al., US2006/0008621 to Gusky et al. and so forth.

Coform air-laid materials are particularly well suited for use in the present invention. Coform nonwoven webs are formed by the comingling of polymeric fibers and absorbent fibers, such as polyolefin fibers and cellulosic fibers, as the fibers are entrained by a common airstream before they are deposited onto a forming surface. Examples of such coform sheets materials, and methods of making the same, are described U.S. Pat. No. 4,100,324 to Anderson et al., U.S. Pat. No. 5,350,624 to Georger et al., and US2011/151596 to Jackson et al., the contents of which are incorporated herein to the extent consistent herewith. In certain embodiments such coform sheets can comprise air-formed matrix of thermoplastic polymeric meltblown fibers and wood pulp fibers. Various suitable materials may be used to provide the polymeric meltblown fibers, such as, for example, polypropylene microfibers. Alternatively, the polymeric meltblown fibers may be elastomeric fibers formed from elastomeric resins such as, for example, VISTAMAXX elastic olefin copolymer resin (available from ExxonMobil Corporation) or KRATON G styrene-ethylene/butylene-styrene and styrene-ethylene/propylene-styrene polymer resins (available from Kraton Performance Polymers, Inc.). Various other suitable polymeric materials, or combinations thereof, may alternatively be utilized to achieve a fibrous sheet having a soft please hand and good cleaning efficacy.

Hydroentangled nonwoven sheet materials are also particularly well suited for use in the present invention. Hydroentangling is a process of forming a nonwoven a web which generally includes the steps of (i) depositing lose fibers on a porous belt or patterned screen and (ii) subjecting the fibers to one or more rows of fine high-pressure jets of water so that the fibers become sufficiently entangled with one another to form a coherent nonwoven web. In certain aspects, hydroentangling readily allows for the combination of different fiber types, such as combining fibers of distinct composition (e.g. polymeric fibers and wood pulp fibers) or fibers of distinct size (e.g. continuous length and staple length fibers). By way of non-limiting example, suitable hydroentangled materials, and methods of making the same, are described in greater detail in U.S. Pat. No. 3,485,706 to Evans, U.S. Pat. No. 3,620,903 to Bunting et al., U.S. Pat. No. 5,009,747 Viazmensky et al., U.S. Pat. No. 5,284,703 to Everhart et al., and U.S. Pat. No. 6,200,669 to Marmon et al, the contents of which are incorporated herein to the extent consistent herewith. It is noted that the category of hydroentangled nonwoven webs includes what is commonly referred to as spunlace fabrics.

By way of further specific examples, the fibrous sheet may comprise a flushable, water dispersible and/or biodegradable sheet material. In certain embodiments, such fibrous sheets may be formed from biodegradable materials and/or binders that will sufficiently degrade when introduced into a sewage system. Various examples of flushable, dispersible and/or degradable nonwoven fibrous materials include, but are not limited to, those described in U.S. Pat. No. 5,667,635 to Win et al; U.S. Pat. No. 6,750,163 Wang et al.; U.S. Pat. No. 6,960,371 to Bunyard et al., and so forth.

If desired, the nonwoven web may also be further treated by one or more techniques as is known in the art to improve the durability, strength, hand, aesthetics, texture, and/or other properties of the fibrous sheet material. For instance, the nonwoven web may be pattern bonded or embossed by the use of heat, pressure and/or ultrasonic energy. By way of non-limiting example, various pattern bonding techniques are described in U.S. Pat. No. 3,855,046 to Hansen et al; U.S. Pat. No. 5,620,779 issued to Levy et al; and U.S. Pat. No. 5,962,112 to Haynes et al., the contents of which are incorporated herein to the extent consistent herewith. The nonwoven fibrous sheet materials may be bonded by continuous and/or discontinuous lines, by patterns of numerous discrete elements, or other patterns as may be desired. As additional examples, the nonwoven web may be bonded along the periphery of the sheet or simply across the width or cross direction of the web adjacent to the edges. Alternatively and/or additionally, a resin, latex or adhesive may be applied to the nonwoven fabric by, for example, spraying or printing, to achieve the desired nature and degree of bonding. The fibrous nonwoven sheets may also, if desired, be treated by various other known techniques such as, for example, stretching, needling, creping, printing, dyeing, and so forth.

Cleaning Composition

As noted herein above, the cleaning composition will at a minimum include (i) a solvent (e.g. water), (ii) insoluble polysaccharide particles, and (iii) surfactant. The individual components of the cleaning composition are selected to present an unstable aqueous dispersion. Thus, in certain embodiments, the cleaning composition of the present invention can include greater than 92.0% water. In certain embodiments, the cleaning composition can include greater than 93.0%, 94.0%, 95.0%, 96.0% or even 97.0% water.

In a further aspect, certain embodiments the cleansing composition can include a combination of water and one or more water soluble alcohols selected form the group consisting of methanol, ethanol, propanol, butanol and pentanol. In such embodiments, the water and alcohol together can comprise greater than 92.0%, 93.0%, 94.0%, 95.0%, 96.0% or even 97.0% of the cleaning composition. Still further, in such embodiments desirably the water comprises at least 2×, and still more desirably, at least 3× the weight percent of alcohol. In still further aspects, in certain embodiments the water:alcohol ratio can be between about 3:1 to about 100:1, or between about 4:1 to about 50:1, or even between about 5:1 to about 20:1.

Particles suitable for use in the present invention include those comprising water insoluble polysaccharides. In certain aspects, the particles may comprise a crystalline and/or birefringent polysaccharide and in still further aspects may comprise non-ionic forms of such polysaccharides. In certain embodiments, it may be desirable for the particles to comprise natural and/or unmodified polysaccharides. Examples of suitable polysaccharide particulates for use in the present invention include, but are not limited to, starch, microcrystalline cellulose, and mixtures thereof. Specific examples of suitable starch particles include natural starch derived from plant sources such as, for example, tapioca, potato, wheat, corn, sorghum, waxy corn, waxy sorghum, millet, mung bean, arrowroot, cassava, taro, fava, and so forth. Desirably, the starch is unmodified and a variety is selected such that it has a gelatinization temperature in excess of 50° C. and, in certain embodiments, in excess of 55° C., 60° C., and even 65° C. In certain embodiments, varieties of natural starch used herein may have a gelatinization temperature below about 90° C. Specific examples of suitable microcrystalline cellulose particles include, but are not limited to, Toshiki SP-White from Nikko Chemicals Co., Ltd, Acticel 12 from Active Organics, Inc., and Avicel/Avicel PH series from FMC Corporation.

The particles can present either a generally round or irregular shape. In a further aspect, the particles are also desirably hydrophilic. In certain aspects, the polysaccharide may have a degree of polymerization between about 200 and about 2500. In still further aspects, the particles may have an average particle size of between about 0.5 and about 100 microns, and still more desirably between about 1 and 75 microns, and still more desirably between about 2 and 50 microns. By average particle size, the present invention means the volume-mean particle size and refers to the diameter of the particle in the aqueous dispersion. For polymer particles that are not spherical, the diameter of the particle is the average of the long and short axes of the particle. Particle sizes can be measured on a Beckman-Coulter LS 13 320 laser-diffraction particle size analyzer or other equivalent device.

The particles comprise less than about 3.0% by weight of the cleaning composition and, in certain embodiments, less than about 2.0% by weight of the cleaning composition. The particles desirably comprise at least about 0.05% by weight of the cleaning composition and, in certain embodiments, greater than about 0.10% by weight of the cleaning composition.

The cleaning composition further includes one or more surfactants. A significant number of surfactants are known for use in cosmetic and/or skin cleaning applications and which are suitable for use with the present invention. The cleaning composition comprises less than 4.0% surfactant, based upon the weight of the cleaning composition. In certain embodiments, the surfactant can comprise less than 3.0% or less than 2.0% of the cleaning composition. The cleaning composition can include at least about 0.05% by weight of the cleaning composition and, in certain embodiments, greater than about 1% by weight of the cleaning composition.

In certain embodiments, the surfactant will comprise one or more nonionic surfactants. By way of examples, suitable classes of nonionic surfactants include, but are not limited to, alkyl glycosides and alkyl polyglycosides, alkyl glucosides and alkyl polyglucosides, ethoxylated alkylphenols, ethoxylated fatty ($C_8$-$C_{22}$) alcohols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof. In certain embodiments, the non-ionic surfactants utilized in the cleaning composition may have an HLB value between 1 and 20, or in a further aspect, between about 3 and about 15. While other types of surfactants may be used in the present invention, nonionic surfactants are believed particularly desirable in certain embodiments since, without being bound to a particular theory, the insoluble particles may include surface charges which would inter-act with ionic surfactants and limit the functionality of either the particle or the ionic surfactant.

Specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_{8-22}$) alcohol, including 3 to 20 ethylene oxide moieties, polyoxyethylene-20 isohexadecyl ether, polyoxyethylene-23 glycerol laurate, PEG 80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and PEG-40 hydrogenated castor oil, PEG-60 hydrogenated castor oil, steareth-2, polysorbate 60, PEG-100 stearate, glyceryl stearate, sorbitan monostearate, polyglyceryl-3 methylglucose distearate, alkyl ($C_{8-22}$) polyglucoside, PEG-26—buteth-26. Combinations of one or more or more of the foregoing nonionic surfactants may also be used in the cleaning composition of the present invention.

One or more anionic, cationic, or zwitterionic surfactants may also be used in the cleaning composition of the present invention, either alone or in combination with other surfactants. By way of non-limiting example, suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids and their metal salts, sulfosuccinates, phosphates, taurates, fatty taurides, fatty acid amide polyoxyethylene sulfates, isethionates, salts of acylamphoacetate, salts of acylamphodipropionate, salts of alkylamphoacetate, salts of alkylamphodiacetate, alkyl aminopropionic acid, sodium coco glycinate, aminopropyl alkylglutamide, sodium alkyliminodipropionate, or combinations thereof. Additionally, suitable zwitterionic surfactants include, but are not limited to, carboxybetaines, sulfobetaines, phosphobetaines, phosphitaines, amine oxides, and derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Specific examples of suitable zwitterionic surfactants include, but are not limited to, cocamidopropyl betaine, coco-betaine; meadofoamamidopropyl betaine, lauryl hydroxy sulfobetaines, lauryl sulfobetaines. Specific examples of suitable cationic surfactants include, but are not limited to, alkyl amine, dimethyl alkyl amine, alkylamido dimethyl propylamine, alkyl aminoethyl imidazoline, alkyl hydroxyethyl imidazoline, tetra alkyl(-aryl) ammonium salts, heterocyclic ammonium salts, alkyl betaines, quaternized APG, ethoxylated alkylamines, esterified quaternary ammonium saltsies, or combinations thereof.

The cleaning composition may, optionally, also include one or more slip agents to alter the hand-feel or skin aesthetics of the formulation. Examples of suitable slip agents include, but are not limited to, polacrylate crosspolymer-6 (e.g. SepiMax Zen), acrylamides copolymer, polyacrylates, bentonite, carbomer, dextrin, xanthan gum, and so forth. The slip agent, when employed, desirably comprises less than 1.0% by weight of the cleaning composition. In certain embodiments, the slip agent may comprise between about 0.75% and about 0.01% by weight of the cleaning composition and, further, between about 0.5% and 0.01% by weight of the cleaning composition.

The cleaning composition may, optionally, also include one or more rheology modifiers to alter the consistency or skin aesthetics of the formulation. Generally, the optimal rheology modifier will modify the target properties of the dispersion without causing the viscosity (at any shear rate) to increase beyond 1000 centipoise at room temperature. In certain embodiments, the cleaning composition has a viscosity (at any shear rate) of between about 1 and 1000 centipoise and, in still further embodiments, between about 10 and about 300 centipoise. Suitable, non-limiting examples of rheology modifiers include gum arabic, carboxymethylcellulose, carboxymethylpropylcellulose, carregeanan, chitosan, cellulose gum, magnesium aluminum silicate, bentonite, hectorite, xanthan gum, guar gum, acrylate copolymer, polyacrylate, polyacrylate crosspolymer, polyquaternium, polyquaternium crosspolymer and so forth. The rheology modifier, when employed, desirably comprises less than 1.0% by weight of the cleaning composition. In certain embodiments, the rheology modifier may comprise between about 0.75% and about 0.01% by weight of the cleaning composition and, further, between about 0.5% and 0.01% by weight of the cleaning composition. It will be appreciated that, as an optional ingredient, in certain embodiments the cleaning composition will not contain any rheology modifiers.

The cleaning composition may, optionally, include one or more preservatives to increase the shelf life of the composition. Suitable preservatives that can be used in the present invention include, but are not limited to, sodium and other metal salts of benzoic acid (e.g. sodium benzoate available under the trade name PUROX S from Emerald Performance Materials); mixtures of methylchloroisothiazolinone and methylisothiazolinone (e.g. KATHON CG from Dow Chemical); methylisothiazolinone (e.g. NELONE 950 from Rohm Haas); DMDM hydantoin and iodopropynyl butylcarbamate (e.g. GLYDANT PLUS from Lonza); hydroxybenzoic acid esters (parabens), such as methylparaben, propylparaben, butylparaben, ethylparaben, benzylparaben, sodium methylparaben, and sodium propylparaben; 2-bromo-2-nitropropane-1,3-diol (e.g. Bronopol from BASF); benzoic acid; sorbic acid and its salts; amidazolidinyl urea (e.g. Germall 115 from Ashlan, Inc.); diazolidinyl urea (e.g. Germall II Ashland, Inc.); and so forth. Combinations of one or more different preservatives are also suitable for use in the present invention. Desirably the preservative is present in the cleaning composition in an amount between about 0.001% and about 2% (by weight of the cleaning composition). In certain embodiments, the preservative may comprise between about 1.0% and about 0.01% by weight of the cleaning composition and, in still further embodiments, may comprise between about 0.5% and 0.1% by weight of the cleaning composition.

The cleaning composition may, optionally, include one or more fragrance components. Common fragrances often comprise water insoluble oils, including essential oils. In addition to the fragrant oil, as is known in the art, it is also common to utilize one or more fragrance solubilizes in order to reduce the tendency of a water insoluble fragrance component to precipitate from the aqueous composition. Examples of fragrance solubilizes include alcohols such as ethanol, isopropanol, benzyl alcohol, and phenoxyethanol; any high HLB (HLB greater than 13) emulsifier, including but not limited to polysorbate; and highly ethoxylated acids and alcohols. Fragrance components, when included, are typically added in amounts less than 0.5% by weight of the cleaning composition and, in certain embodiments, between about 0.1% and 0.01% by weight of the cleaning composition.

The cleaning composition may, optionally, further include one or more skin benefit agents such as, for example, antioxidents, astringents, conditioners, emollients, deodorants, external analgesics, film formers, humectants, hydrotropes, pH modifiers, surface modifiers, skin protectants, and so forth. By way of example, suitable humectants include but are not limited to glycerin, glycerin derivatives, sodium hyaluronate, betaine, amino acids, glycosaminoglycans, sorbitol, glycols, polyols, sugars, hydrogenated starch, hydrolysates, and mannose, propylene glycol, sodium PCA, trehalose, urea, lactic acid and its salts, hydroxyethylurea, and other appropriate ingredients. By way of non-limiting example, suitable skin conditioners include aloe-vera, betaine, lactic acid, panthenol, Camellia Sinensis leaf extract, Chamomilla Recutita flower extract, rose extract, Cananga Odorata flower extract, Prunus Serrulata flower extract, PEG-50 Shea butter, and other appropriate ingredients. In addition, suitable emollients include, but are not limited to, mineral oil, dimethicone, dimethicone copolyol, cyclosiloxane, ehtylhexyl palmitate, ethylhexyl stearate, cetyl ethylhexanoate, hexanediol, hydrogenated polydecene, hydrogenated polydidecene, lanolin, cocoglycerides, caprylic/capric triglyceride, and so forth.

When employed, the skin benefit agents desirably comprise less than 2.0% by weight of the cleaning composition. In certain embodiments, the skin benefit agent may comprise between about 1.0% and about 0.01% by weight of the cleaning composition and, further, between about 0.5% and 0.05% by weight of the cleaning composition. However, when utilizing one or more skin benefit agents, the selection and addition of any such component should not cause the viscosity of the cleaning composition to exceed 1000 centipoise. In this regard the cleaning composition desirably has a room temperature viscosity (at any shear rate) of between 1 and 1000 centipoise and, in still further embodiments, between about 10 and about 300 centipoise.

With respect to each of the optional ingredients discussed herein above, it will be appreciated that in certain embodiments the cleaning composition will not contain any one of such optional ingredients or even lack all of such optional ingredients.

Wet Wipe Composition

The cleaning composition is incorporated into the porous sheet to from a wet wipe. Desirably, the cleaning formulation is added to the fibrous sheet in an add-on amount of from about 50% to about 600% (by weight of the dry porous sheet), more desirably from about 75% to about 500% (by weight of the dry porous sheet), even more desirably from about 100% to about 400% (by weight of the dry porous sheet), and especially more desirably from about 100% to about 350% (by weight of the dry porous sheet).

The cleaning composition, as an unstable dispersion, is desirably mixed and/or agitated immediately prior to the addition of the cleaning composition in order to maintain a substantially homogeneous dispersion. More desirably, the cleaning composition is continuously agitated up through and until added to the fibrous sheet. In certain aspects, cleaning composition and porous sheets can both be agitated during and/or for a short period after application of the cleaning composition to the porous sheet. The mixing and/or agitation of the dispersion may be accomplished through the use of an agitator and/or homogenizer. The cleaning composition may be added to individual sheets or, alternatively, be applied to a stack of fibrous sheets. After application of the cleaning composition to the fibrous sheet(s), the wet wipes are desirably sealed in a suitable container in order to maintain the desired level of moisture content over time.

Importantly, the temperature of the aqueous liquid should be below the gelatinization temperature, more desirably at least 5° C. below the gelatinization temperature, when the particles are added to the aqueous liquid and thereafter during the formation of the aqueous dispersion and impregnation of the porous sheet(s). In addition, while it is often advantageous to use heat to aid in the formation of an aqueous solution including the water and surfactant, in such instances the aqueous solution should be cooled to a temperate below the gelatinization temperature, desirably at least 5° C. below the gelatinization temperature, prior to the subsequent addition of the polysaccharide particles.

The wet wipes can be maintained over time in a sealed container such as, for example, plastic pouches or bags, canisters, jars, tubs, buckets and so forth. Desirably the stacked wet wipes are maintained in a resealable container. When utilizing a stack of wet wipes the use of a resealable container is particularly desirable in order to limit evaporation of the cleaning composition from the remaining unused wet wipes in the container. Exemplary resealable containers and wet wipe dispensers include, but are not limited to, those described in U.S. Pat. No. 4,171,047 to Doyle et al., U.S. Pat. No. 4,353,480 to McFadyen, U.S. Pat. No. 4,778,048 to Kaspar et al., U.S. Pat. No. 4,741,944 to Jackson et al., U.S. Pat. No. 6,705,565 Newman et al., and US2012/0160864 to Shoaf et al., the contents of which are incorporated herein to the extent consistent herewith. Flexible bag packaging with a resealable label are particularly well suited for use with the present invention and examples of the same include, but is not limited to, those described in U.S. Pat. No. 5,264,265 to Kaufmann, US2005/0011906 to Buck et al., US2010/0154264 to Scott et al., and US2010/0155284 to Gerstle et al., the contents of which are incorporated herein to the extent consistent herewith.

As is known in the art, the sheets can be incorporated or oriented in the container as desired and/or folded as desired in order to improve efficiency of use and/or dispensing as is known in the art. In certain embodiments, stacks of wet wipes are desirably arranged and combined with a dispenser to facilitate one at a time dispensing. The sheets may be inter-folded in various know overlapping configurations such as, for example, V-folds, Z-folds, W-folds, quarter-folds and so forth. Equipment and processes for forming dispensable stacks of wipes are known in the art; examples of which include, but are not limited to, those described in U.S. Pat. No. 3,401,927 to Frick et al.; U.S. Pat. No. 4,502,675 to Clark et al.; U.S. Pat. No. 5,310,398 to Yoneyama, U.S. Pat. No. 6,612,462 to Sosalla et al., and so forth. With respect to product formats utilizing a continuous length of sheet material, such as in certain rolled formats, the individually separable wet wipes desirably have perforated or over-bonded lines of weakness which allow separation into smaller individual sheets of a desired shape and size. The particular stack height and sheet count can vary with the intended format and use. However, in certain embodiments, the stack may include between 3 and 250 wet wipes and, in further embodiments may include between about 10 and 150 wet wipes and in still further embodiments may include between about 10 and 90 wet wipes. The edge of the wipes may also be modified in one or more aspects, as desired, to improve the user's ability to remove individual wipes form a stack such as, for example, as described in U.S. Pat. No. 7,078,087 to Romano et al.

The wet wipes can, optionally, include one or more additional elements or components as are known in the art. Thus, while the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

Method for Determining Gelatinization Temperature

The gelatinization temperature for the polysaccharide particles, such as starch, is determined using the electrical conductivity method. In this regard, the electrical conductivity of aqueous starch suspensions increases linearly with temperature except for the range overlapping gelatinization. This phenomena, and use of the same to determine gelatinization temperature, is described in greater detail in the following articles: Li et al., *Determination of Starch Gelatinization Temperature by Ohmic Heating*, Journal of Food Engineering 62, 113-12-(2004) and Ubwa et al., *Studies on the Gelatinization Temperature of Some Cereal Starches*, International Journal of Chemistry, vol. 4, No. 6 (2012).

125 $cm^3$ of distilled water is poured into a 250 $cm^3$ wide-mouthed flask (reaction vessel) and is suspended in a 1000 $cm^3$ Pyrex beaker containing water (water bath). A magnetic stirrer is located within the reaction vessel in order to prevent stratification of the particles. The water bath is placed upon a hot plate which is adjusted to provide a 1 degree Celsius rise in temperature per minute. Temperature and conductivity probes are placed within the reaction vessel. When the temperature of the reaction vessel reaches 40° C., 0.5 g of the particles is added to 25 $cm^3$ of distilled water (at room temperature), stirred to form a suspension and then slowly poured into the reaction vessel. The conductivity and temperature of the reaction vessel are measured at 5 second intervals until the temperature of the reaction vessel reaches 90° C. or until the gelatinization is complete (whichever is higher). Plotting current versus time will yield a generally linear increase in current over time, however at the onset of gelatinization the current will decrease until gelatinization is complete at which point the current will again increase linearly with temperature. The gelatinization temperature for purposes herein means the temperature at which gelatinization begins which, with respect to the plot of time versus current, will be represented by the initial inflection point.

What is claimed is:

1. A wet wipe comprising:
a porous sheet comprising a coherent web of fibers;
a cleaning composition contained within said porous sheet, said cleaning composition contained within said porous sheet in an amount between 50% and 600% based upon the dry weight of said porous sheet;
said cleaning composition comprising, based upon the weight of the cleaning composition, (i) greater than 92.0% water, (ii) between 4% and 0.05% surfactant, and (iii) between about 3.0% and about 0.05% water insoluble polysaccharide particles and wherein said particles reside on the surface of the fibers of said porous sheet.

2. The wet wipe of claim 1 wherein the polysaccharide is a natural and unmodified polysaccharide selected from the group consisting of starch and microcrystalline cellulose.

3. The wet wipe of claim 2 wherein water comprises at least 95% of the cleaning composition and further wherein the surfactant comprises between 2.0% and 0.05% of the cleaning composition.

4. The wet wipe of claim 2 wherein the particles have a particle size between about 1 and about 100 microns.

5. The wet wipe of claim 1 wherein the polysaccharide is selected from the group consisting of birefringent polysaccharides and non-ionic polysaccharides.

6. The wet wipe of claim 5 the polysaccharide comprises a starch having a gelatinization temperature in excess of 50° C.

7. The wet wipe of claim 6 wherein the polysaccharide is a starch selected from the group consisting of tapioca, potato, wheat, corn, sorghum, millet, mungbean, rice, cassava, arrowroot, oca, taro, and fava.

8. The wet wipe of claim 6 wherein the cleansing composition has a viscosity between about 1 and 300 centipoise.

9. The wet wipe of claim 5 wherein the surfactant contained within the cleaning composition is selected from the group consisting of non-ionic surfactants.

10. The wet wipe of claim 5 wherein the cleaning composition further includes between 1.0% and 0.05% of a slip agent.

11. A wet wipe comprising:
a porous sheet comprising a coherent web of fibers;
a cleaning composition contained within said porous sheet, said cleaning composition contained within said porous sheet in an amount between 50% and 600% based upon the dry weight of said porous sheet;
said cleaning composition comprising, based upon the weight of the cleaning composition, (i) water, (ii) a water soluble alcohol selected form the group consisting of methanol, ethanol, propanol, butanol and pentanol, (iii) between 4% and 0.05% surfactant, and (iv) between about 3.0% and about 0.05% water insoluble polysaccharide particles and,
wherein said water and said alcohol together comprise greater than 92% by weight of the cleaning composition, and
wherein the ratio of water to alcohol is between 3:1 and 100:1, and further
wherein the particles reside on the surface of the fibers of said porous sheet.

12. The wet wipe of claim 11 wherein the polysaccharide is a natural and unmodified polysaccharide selected from the group consisting of starch and microcrystalline cellulose.

13. The wet wipe of claim 11 wherein the polysaccharide comprises a non-ionic polysaccharide and further wherein the surfactant in the cleaning composition is selected from the group consisting of non-ionic surfactants.

14. The wet wipe of claim 11 wherein water and alcohol together comprise at least 95% of the cleaning composition and further wherein the surfactant comprises between 2.0% and 0.05% of the cleaning composition.

15. The wet wipe of claim 11 wherein the polysaccharide comprises an unmodified starch having a gelatinization temperature in excess of 50° C.

16. The wet wipe of claim 15 wherein the cleansing composition has a viscosity between about 1 and 300 centipoise and further wherein the particles have a particle size between about 1 and about 100 microns.

17. The wet wipe of claim 16 wherein the cleaning composition further includes between 1.0% and 0.05% of a slip agent.

18. A method of making a wet wipe comprising the steps of:
providing a fibrous sheet;
providing an unstable aqueous dispersion comprising, by weight of the dispersion, (i) greater than 92% water; (ii) 0.05-3% water insoluble polysaccharide particles; and (iii) 0.05-4% surfactant;
mixing said unstable aqueous dispersion to generate a substantially homogenous aqueous dispersion;
applying said substantially homogenous aqueous dispersion to said fibrous sheet in an amount between about 50% and 600% based upon the dry weight of said fibrous sheet, thereby forming a wet wipe; and
sealing said wet wipes in a container.

19. The method of claim 18 wherein the polysaccharide comprises a starch having a gelatinization temperature in excess of 50° C. and further wherein the dispersion is maintained at a temperature at least about 5° C. below said gelatinization temperature.

20. The method of claim 18 wherein the polysaccharide comprises a starch having a gelatinization temperature in excess of 50° C. and further comprising the steps of
adding the surfactant to the water under heat to form an aqueous solution,
cooling the aqueous solution to a temperature at least 5° C. below the gelatinization temperature, and then
adding the particles to the aqueous solution to form an aqueous dispersion and thereafter maintaining the temperature of the aqueous dispersion at least about 5° C. below said gelatinization temperature.

* * * * *

UNITED STATES PATENT AND TRADEMARK OFFICE
CERTIFICATE OF CORRECTION

PATENT NO. : 10,166,174 B2
APPLICATION NO. : 15/101382
DATED : January 1, 2019
INVENTOR(S) : Cunningham et al.

Page 1 of 1

It is certified that error appears in the above-identified patent and that said Letters Patent is hereby corrected as shown below:

In the Claims

Claim 1, Column 11, Line 62 after the word "said" insert --cleaning composition is an unstable dispersion and further wherein said--

Claim 11, Column 12, Line 45 between the words "the" and "particles" insert --cleaning composition is an unstable dispersion and the--

Signed and Sealed this
Twenty-sixth Day of February, 2019

Andrei Iancu
*Director of the United States Patent and Trademark Office*